United States Patent

Baasner et al.

[11] Patent Number: 5,057,142
[45] Date of Patent: Oct. 15, 1991

[54] HERBICIDAL THIAZOLECARBOXAMIDE DERIVATIVES

[75] Inventors: Bernd Baasner, Bergisch Gladbach; Michael Schwamborn, Cologne; Hans-Joachim Santel, Leverkusen; Klaus Lürssen; Robert R. Schmidt, both of Bergisch Gladbach, all of Fed. Rep. of Germany

[73] Assignee: Bayer Aktiengesellschaft, Leverkusen, Fed. Rep. of Germany

[21] Appl. No.: 587,283

[22] Filed: Sep. 24, 1990

[30] Foreign Application Priority Data

Oct. 13, 1989 [DE] Fed. Rep. of Germany ....... 3934197

[51] Int. Cl.$^5$ .................. C07D 277/56; A01N 43/78
[52] U.S. Cl. ........................................ 71/90; 544/331; 544/333; 546/280; 548/184; 548/188
[58] Field of Search ............... 548/188, 184; 71/90; 546/280; 544/331, 333

[56] References Cited

U.S. PATENT DOCUMENTS 4,336,389 6/1982 Howe .................. 548/201

Primary Examiner—Robert Gerstl
Attorney, Agent, or Firm—Sprung, Horn, Kramer & Woods

[57] ABSTRACT

Herbicidal thiazolecarboxamide derivatives of the formula

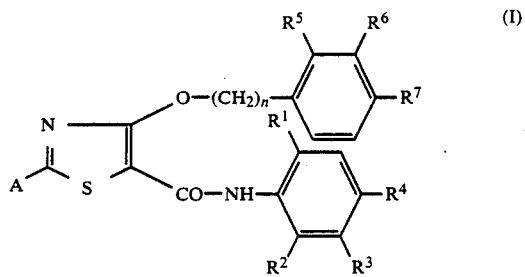

in which
n represents the numbers 0 or 1,
A represents in each case optionally substituted alkyl, aryl, heteroaryl, arylamino or heteroarylamino,
$R^1$ represents hydrogen, halogen or alkyl,
$R^2$ represents hydrogen, halogen or alkyl,
$R^3$ represents hydrogen, halogen, alkyl or halogenoalkyl,
$R^4$ represents hydrogen, halogen, alkyl or halogenoalkyl,
$R^5$ represents hydrogen, halogen, alkyl, nitro or amino,
$R^6$ represents hydrogen, halogen, alkyl halogenoalkyl, alkoxy, halogenoalkoxy, alkylthio, halogenoalkylthio or alkoxycarbonyl, and
$R^7$ represents hydrogen, halogen, alkyl, nitro or amino 9 Claims, No Drawings

HERBICIDAL THIAZOLECARBOXAMIDE DERIVATIVES

The invention relates to new thiazolecarboxamide derivatives, to a process and to new intermediates for their preparation, and to their use as herbicides.

It is already known that certain pyridine-3-carboxamides (nicotinamides) have herbicidal properties. N-(2,4-difluorophenyl-2-(3-trifluoromethyl-phenoxy)-3-pyridinecarboxamide (DIFLUFENICAN), in particular, has gained importance from amongst this group (cf. EP-A 53,011). Similar N-aryl-2-phenoxy-nicotinamides having a herbicidal activity are known from U.S. Pat. No. 4,270,946. However, the action against weeds and the tolerance in wheat is not entirely satisfactory with these compounds.

New thiazolecarboxamide derivatives have now been found, of the general formula (I)

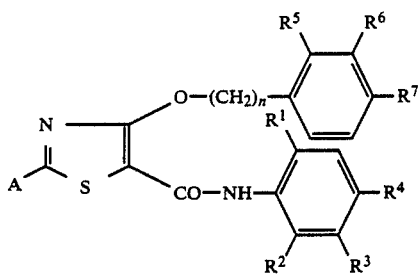

in which
  n represents the numbers 0 or 1,
  A represents in each case optionally substituted alkyl, aryl, heteroaryl, arylamino or heteroarylamino,
  $R^1$ represents hydrogen, halogen or alkyl,
  $R^2$ represents hydrogen, halogen or alkyl,
  $R^3$ represents hydrogen, halogen, alkyl or halogenoalkyl,
  $R^4$ represents hydrogen, halogen, alkyl or halogenoalkyl,
  $R^5$ represents hydrogen, halogen, alkyl, nitro or amino,
  $R^6$ represents hydrogen, halogen, alkyl, halogenoalkyl, alkoxy, halogenoalkoxy, alkylthio, halogenoalkylthio or alkoxycarbonyl, and
  $R^7$ represents hydrogen, halogen, alkyl, nitro or amino.

Furthermore, it has been found that the thiazolecarboxamide derivatives of the general formula (I) are obtained when thiazolecarboxylic acid halides of the formula (II)

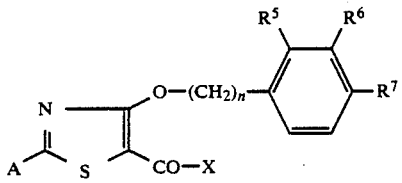

in which
  n, A, $R^5$, $R^6$ and $R^7$ have the abovementioned meanings and
  X represents halogen,
are reacted with aniline derivatives of the general formula (III)

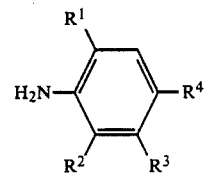

in which
  $R^1$, $R^2$, $R^3$ and $R^4$ have the abovementioned meanings,
if appropriate in the presence of a diluent and if appropriate in the presence of an acid acceptor.

Finally, it has been found that the new thiazolecarboxamide derivatives of the formula (I) have herbicidal, in particular selective-herbicidal, properties.

Surprisingly, the new compounds of the formula (I) have better herbicidal actions and are better tolerated by crop plants than the class of the nicotinamides, which is very closely related structurally and which also includes diflufenican which is mentioned above.

Formula (I) provides a general definition of the new thiazolecarboxamide derivatives. Preferred compounds of the formula (I) are those in which
  n represents the numbers 0 or 1,
  A represents $C_1$-$C_{10}$-alkyl, phenyl, 5-membered hetero
  aryl having one O, one S, one N atom, one N and one O atom or one S atom or having 2 N atoms, or represents 6-membered heteroaryl having 1-3 N atoms, or represents phenylamino, pyridylamino or pyrimidinylamino, it being possible for these radicals to be substituted by halogen or (with the exception of alkyl) by $C_1$-$C_4$-alkyl,
  $R^1$ represents hydrogen, fluorine, chlorine or $C_1$-$C_4$-alkyl,
  $R^2$ represents hydrogen, fluorine, chlorine or $C_1$-$C_4$-alkyl,
  $R^3$ represents hydrogen, fluorine or chlorine, or represents $C_1$-$C_4$-alkyl which is optionally monosubstituted or polysubstituted by fluorine and/or chlorine,
  $R^4$ represents hydrogen, fluorine or chlorine, or represents $C_1$-$C_4$-alkyl which is optionally monosubstituted or polysubstituted by fluorine and/or chlorine,
  $R^5$ represents hydrogen, fluorine, chlorine, $C_1$-$C_4$-alkyl, nitro or amino,
  $R^6$ represents hydrogen, fluorine or chlorine, or represents $C_1$-$C_4$-alkyl, $C_1$-$C_4$-alkoxy or $C_1$-$C_4$-alkylthio, each of which is optionally monosubstituted or polysubstituted by fluorine and/or chlorine, or represents $C_2$-$C_5$-alkoxycarbonyl, and
  $R^7$ represents hydrogen, fluorine, chlorine, $C_1$-$C_4$-alkyl, nitro or amino.

Particularly preferred thiazolecarboxamide derivatives of the formula (I) are those in which
  n represents the numbers 0 or 1,
  A represents $C_1$-$C_3$-alkyl, phenyl, furanyl, thienyl, pyrrolyl, thiazolyl, oxazolyl, pyrazolyl, imidazolyl, pyridyl, pyrimidinyl, phenylamino, pyridylamino or pyrimidinylamino, it being possible for these radicals to be substituted by fluorine or chlorine or (with the exception of alkyl) by methyl or ethyl;
  $R^1$ represents hydrogen, fluorine, chlorine, methyl or ethyl, $R^2$ represents hydrogen, fluorine, chlorine, methyl or ethyl, $R^3$ represents hydrogen, fluorine or chlorine, or represents methyl or ethyl, each of which is optionally substituted by fluorine or chlorine, $R^4$ represents hydrogen, fluorine or chlorine, or represents methyl or ethyl, each of which is optionally substituted by fluorine or chlorine, $R^5$ represents hydrogen, fluorine, chlorine, methyl, ethyl, nitro or amino, $R^6$ represents hydrogen, fluorine or chlorine, or represents methyl, ethyl, methoxy, ethoxy, methylthio or ethylthio, each of which is optionally substituted by fluorine or chlorine, or represents methyoxycarbonyl or ethoxycarbonyl, and $R^7$ represents hydrogen, fluorine, chlorine, methyl, ethyl, nitro or amino.

If, for example, 2-methyl-4-(3-trifluoromethylphenyloxy)-thiazole-5-carbonyl chloride and 2,4-difluoroaniline are used as starting substances, the course of the reaction of the process according to the invention can be represented by the following equation:

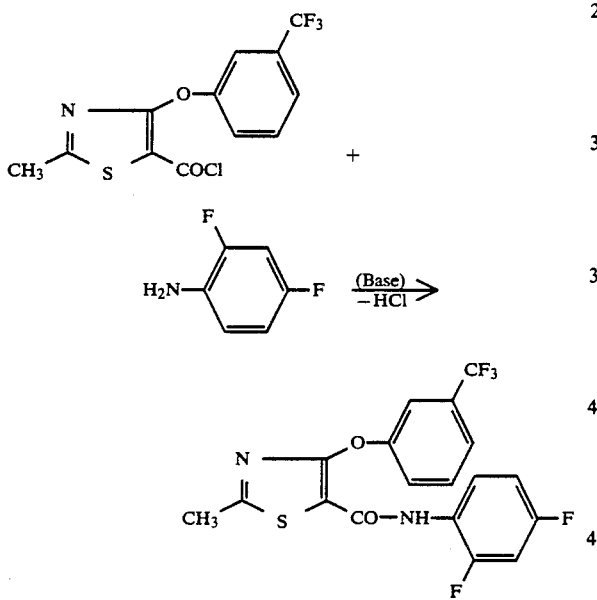

The process according to the invention for the preparation of the new compounds of the general formula (I) is preferably carried out using diluents. Suitable diluents for this purpose are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylene sulphone and hexamethylphosphoric triamide.

Acid acceptors which can be employed in the process according to the invention for the preparation of the compounds (I) are all acid-binding agents which can customarily be used for reactions of this type. The following are preferably suitable: alkali metal hydroxides, such as, for example, sodium hydroxide and potassium hydroxide, alkaline earth metal hydroxides, such as, for example, calcium hydroxide, alkali metal carbonates and alkali metal alcoholates, such as sodium carbonate, potassium carbonate, sodium methylate, sodium ethylate, potassium methylate and potassium ethylate, furthermore aliphatic, aromatic or heterocyclic amines, for example triethylamine, trimethylamine, dimethylaniline, dimethylbenzylamine, pyridine, quinoline, 1,5-diazabcyclo-[4,3,0]-non-5-ene (DBN), 1,8-diazabicyclo-[5,4,0]-undec-7-ene (DBU) and 1,4-diazabicyclo-[2,2,2]-octane (DABCO). It is also possible to employ the anilines of the formula (III) in excess and to allow the excess aniline to act as the acid binder.

In the process according to the invention for the preparation of the compounds (I), the reaction temperatures are between 0° C. and reflux temperature, which is determined by the diluent used and/or the aniline derivative (III) employed as the starting material. It is preferred to carry out the process at temperatures between 20° C. and 140° C.

In general, the reactions are carried out under atmospheric pressure. However, it is also possible to carry out the reactions in sealed vessels and under elevated pressure.

When carrying out the process according to the invention, 1.0 to 1.6 moles, preferably 1.05–1.30 mole, of aniline derivative (III) and 1 to 3 moles, preferably 1 to 2 moles, of acid acceptor or another mole of the aniline of the formula (III) are employed per mole of thiazolecarboxylic acid halide (II).

The reaction mixture is worked up by customary methods. If required or desired, the reaction products can also be purified by customary methods of organic chemistry (crystallization; distillation at atmospheric pressure or under reduced pressure; chromatography).

Formula (II) provides a general definition of the thiazolecarboxylic acid halides required as starting materials for carrying out the process according to the invention. In this formula (II), n, A, $R^5$, $R^6$ and $R^7$ preferably, or particularly preferably, have those meanings which have already been mentioned above in connection with the description of the compounds of the formula (I) according to the invention as being preferred, or particularly preferred, for n, A, $R^5$, $R^6$ and $R^7$, and X preferably represents fluorine, chlorine or bromine, particularly preferably chlorine or bromine.

The thiazolecarboxylic acid halides of the formula (II) here hitherto unknown. These intermediates (II), which are new and valuable, are likewise a subject of the invention.

The new compounds of the formula (II) are obtained by a new process in three stages, by a) reacting, in a first stage, a 4-hydroxythiazole derivative of the formula (IV) or an alkali metal salt thereof (IVa)

(IV, IVa)

in which

A has the abovementioned meaning, $R^8$ represents alkyl (preferably having 1–4 C atoms, particularly preferably, methyl or ethyl), and Z represents hydrogen (=IV) or Z represents sodium or potassium (=IVa), with an aromatic halogen compound of the formula (V)

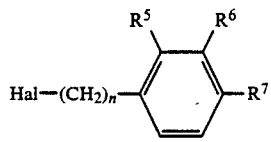

in which n, $R^5$, $R^6$ and $R^7$ have the abovementioned meanings and

Hal represents halogen (preferably fluorine, chlorine or bromine, particularly preferably fluorine or chlorine), if appropriate in the presence of a diluent and if appropriate in the presence of an acid acceptor, then b) converting the thiazolecarboxylic esters, prepared in stage (a), of the formula (VI)

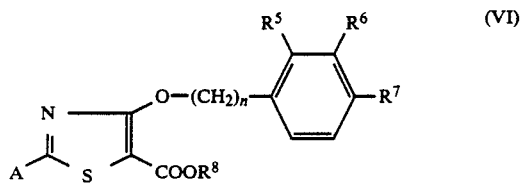

in which

A, n, $R^5$, $R^6$, $R^7$ and $R^8$ have the abovementioned meanings, by a customary hydrolysis reaction into the free thiazolecarboxylic acids of the formula (VII)

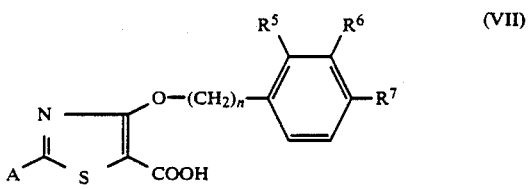

in which

A, n, $R^5$, $R^6$ and $R^7$ have the abovementioned meanings, and finally c) converting, in a third stage, the thiazolecarboxylic acids, prepared in stage (b), of the formula (VII) with suitable halogenating agents into the corresponding thiazolecarboxylic acid halides of the above formula (II).

What follows now is more detailed information on the reaction stages (a), (b) and (c):

Re Stage (a)

The starting compounds of the formulae (IV) and (IVa) are known (cf. Gazz. Chim. Ital. 93 p. 215–220 (1963)), or they can be prepared in analogy to the methods described in this publication. The alkali metal salts (IVa) are obtained from the hydroxy compounds (IV) by reaction with alkali metal hydroxides or alkali metals. The salts (IVa) can either be prepared in a specific manner and employed in pure, isolated form, or else can be generated in situ before or during the reaction with the halogen compounds (V).

The halogen compounds of the formula (V), that is to say halogenobenzenes and benzyl halides, are generally known compounds of organic chemistry. In the event that, in (V), n=0, a halogenobenzene which has been activated (for example by a nitro group) must be employed (see below).

It is preferred to carry out the reactions in the presence of a diluent and in the presence of an acid acceptor. The diluents and acid acceptors suitable for this purpose are in principle the same as described above in connection with the procedure of the process according to the invention for the preparation of the end products (I). N-Methylpyrrolidone may be mentioned as a particularly favorable diluent.

The reaction temperatures are between 0° C. and reflux temperature, which is determined by the diluent used and/or by the halogen compound (V) employed in each case. It is preferred to carry out the process at temperatures of between 40° C. and 240° C.

In general, the reactions are carried out under atmospheric pressure; however, they can also be effected in sealed vessels under elevated pressure.

The reaction times are between about 30 minutes and 72 hours; the course of the reaction can be monitored easily by means of analytical methods (for example thin-layer chromatography, gas chromatography).

When the reaction is carried out, the compounds (IV)/(IVa) and (V) are generally employed in equimolar amounts. However, it is also possible to use an excess of one or the other starting component, but not more than 20% for economic reasons.

Working-up is carried out by customary methods, such as aqueous extraction working-up, crystallization, distillation and/or preparative chromatography.

Re Stage (b)

The hydrolysis can be carried out in acid or basic medium using the hydrolysis processes customary in organic chemistry. The hydrolysis is carried out particularly advantageously using basic agents, by dissolving the compounds of the formula (VI) in an inert organic solvent (preferably in an alcohol, particularly preferably in methanol or ethanol), and adding the base (preferably sodium hydroxide or potassium hydroxide) which is dissolved in water, in methanol or in ethanol.

When carrying out the hydrolysis, at least the equimolar amount of a base is employed per mole of thiazolecarboxylic ester (VI); however, it is more advantageous to use an excess of base (up to 25 moles, preferably up to 10 moles, particularly preferably of about 5 moles on financial grounds).

The reaction temperatures are between 0° C. and the reflux temperature of the solvent used, preferably between 5° and 60° C.

The reaction times are between about 30 minutes and 24 hours. The reaction can easily be monitored by means of thin-layer chromatography or gas chromatography and can be terminated as soon as the precursor (VI) has reacted quantitatively.

Working-up can be effected by customary methods, for example by removing the volatile constituents—if appropriate under reduced pressure—, taking up the residue in water, removing any impurities which may be present by means of extraction (for example with dichloromethane) and precipitating the free thiazolecarboxylic acids (VII) by acidifying the aqueous phase; the acids (VII) can be separated by filtration, dried and, if required, purified by recrystallization.

Re Stage (c)

The free acids (VII) can be converted into the acid halides (II, where X=Cl or Br) with the aid of the customary halogen-transfer agents. Suitable for this purpose are, for example, simple carboxylic acid halides (such as acetyl chloride or acetyl bromide and benzoyl chloride or benzoyl bromide) or inorganic acid halides (such as phosphorus pentachloride, phosphorus trichloride or phosphorus tribromide or thionyl chloride).

To prepare the compounds of the formula (II, where X=Cl), it is particularly advantageous to use thionyl chloride (SOCl₂). To this end, the carboxylic acids (VII) are dissolved in an organic solvent which is inert under the reaction conditions (dichloromethane being particularly preferred) and reacted, or reacted undiluted, with an at least equimolar amount of thionyl chloride; however, it is advantageous to employ an excess of thionyl chloride (up to 5 moles, preferably 1.5-2 moles per mole of (VII)). Furthermore, it can be advantageous to add a catalyst, such as dimethylformamide (DMF).

The reaction temperatures are between 0° C. and the reflux temperature of the solvent used in each case. The reaction is complete when the evolution of gas has ceased.

Working-up can be carried out by customary methods: Volatile constituents are removed by distillation under atmospheric pressure or reduced pressure; the residue can be purified further by recrystallization or chromatography. However, the acid chlorides (II) are usually obtained in a purity which suffices for the subsequent reaction with the aniline derivatives (III) to give the end products (I).

More Information on Stage (a)

In the event that it is intended to prepare 4-phenoxythiazolecarboxylic esters of the formula (VI, where n=0) where R⁶ for example represents CF₃, by process stage (a) it is necessary to employ an activated compound of the type (V, where n=0) for the reaction with a compound of the formulae (IV) and (IVa), respectively.

For example, a compound (Va) which is activated by a nitro group is employed to prepare a compound of the type (VIa) by reaction with a compound of the formula (IVa), according to the equation below:

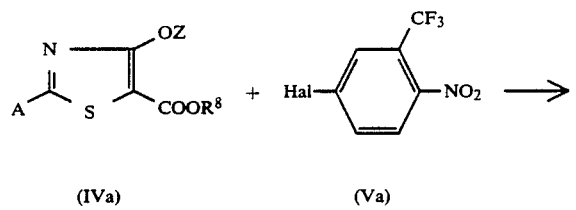

(IVa)    (Va)

(where Z for example represents Na and Hal for example represents F)

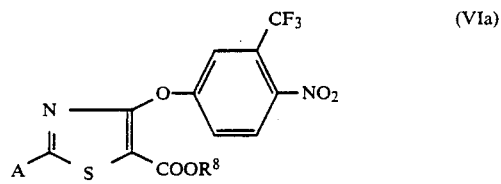

(VIa)

To obtain end products of the type (I) where n=0, R⁶=CF₃ and R⁵=R⁷=H, it is now necessary to remove the nitro group in a customary reaction sequence (hydrogenation —NO₂→—NH₂, diazotization, boiling), advantageously at the intermediate stage (VIa), followed by the reaction stages (b) and (c) and the subsequent reaction of (II) with (III).

To this end, nitro compounds of the formula (VIa) are initially converted in a first stage (α) into the amines of the formula (VIb) by means of a customary hydrogenation reaction:

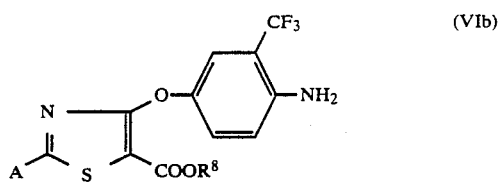

(VIb)

In the amino compounds (VIb), the amino group can subsequently be removed by reaction sequence (β)—diazotization and boiling—and replaced by an H atom, the desired intermediates of the type (VIc) being obtained,

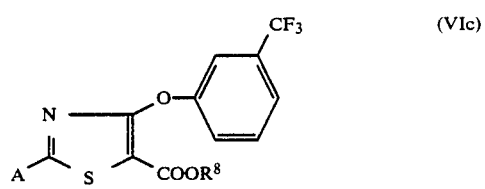

(VIc)

which can be further reacted as described above to give corresponding end products (I).

If appropriate, the hydrogenation (α) is effected in the presence of an organic solvent and in the presence of a suitable hydrogenation catalyst, using hydrogen.

The following may be mentioned as examples of solvents for the hydrogenation of stage (α): alcohols, such as methanol, ethanol, propanol, n-butanol and tert-.butanol, and ethers, such as tetrahydrofuran and dioxane.

Methanol and/or ethanol are preferably employed.

Examples of hydrogenation catalysts which can be used are metal, or noble metal, catalysts, such as platinum, platinum oxide, palladium, palladium oxide, Raney nickel, nickel, Raney cobalt, palladium/barium carbonate and platinum/barium sulphate; platinum, palladium and Raney nickel are preferably employed.

The hydrogenation (α) can be carried out for example at a pressure of 1 to 100 bar, preferably of 1 to 80 bar, particularly preferably of 10 to 60 bar.

In general, the hydrogenation temperature can be 20°-120° C., preferably 20°-100° C., particularly preferably 20°-80° C.

The resulting amino compounds (VIb) can be purified by customary methods (such as crystallization, distillation and/or chromatography).

Diazotization and boiling ($\beta$) are effected by customary methods of organic chemistry (cf., for example, the summary of diazotization processes in: Houben-Weyl, Methoden der Organischen Chemie [Methods of Organic Chemistry], Vol X/3, p. 12-38; Georg-Thieme-Verlag, Stuttgart 1965).

Thus, the diazotization can be carried out in aqueous mineral acid, using sodium nitrite ($NaNO_2$). An equimolar amount of $NaNO_2$ and an excess of mineral acid, preferably concentrated hydrochloric acid (excess up to 25 moles), are employed per mole of amino compound (VIb), at temperatures of from $-10°$ to $+50°$ C.

However, the diazotization can also be carried out in organic solvents, using nitric esters (that is to say, alkyl nitrites, such as methyl nitrite or isoamyl nitrite).

The resulting reaction solution can subsequently be "boiled", resulting in the amino-group-free compounds of the type (VIc) (cf. the relevant summary in: Houben-Weyl, Methoden der Organischen Chemie [Methods of Organic Chemistry], Vol. X/3, p. 115-144; Georg-Thieme-Verlag, Stuttgart 1965).

It is particularly advantageous to add ethanol (10 to 25 times the starting volume) to the previously obtained diazonium salt in the diazotization solution, and to reflux the mixture. Subsequent working-up is carried out by customary methods, and the crystalline crude products are purified by chromatography and/or recrystallization.

This may be followed by the above-described process stages (b) and (c) and the preparation of the end products [according to the reaction (II)+(III)→(I)].

Formula (III) provides a general definition of the aniline derivatives furthermore required as starting materials for carrying out the process according to the invention for the preparation of the end products. In this formula (III), the radicals $R^1$-$R^4$ preferably, or particularly preferably, have those meanings which have already been mentioned above in connection with the description of the end products (I) as being preferred, or particularly preferred, for $R^1$, $R^2$ $R^3$ and $R^4$.

Most of the aniline derivatives (III) are known; individual compounds from this group which have not previously been described can be prepared in analogy to the anilines which are known.

More details concerning the preparation of the intermediates and end products can be seen from the Preparation Examples.

The active compounds of the formula (I) according to the invention can be used as defoliants, desiccants, agents for destroying broad-leaved plants and, in particular, as weedkillers. By weeds, in the broadest sense, there are to be understood all plants which grow, in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial crops, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf, meadows and pastures, and for the selective combating of weeds in annual cultures.

The compounds of the formula (I) according to the invention are suitable for selectively combating monocotyledon and dicotyledon weeds, in particular in monocotyledon crops using the pre-emergence method.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable:

for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable components for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N,-dimethyl-urea (METABENZTHIAFURON) for combating weeds in cereals; 4-amino-3-methyl-6-phenyl-1,2,4-triazin-5(4H)-one (METAMITRON) for combating weeds in sugar beets and 4-amino-6-(1,1-dimethylethyl)-3-methylthio-1,2,4-triazin(5(4H)-one (METRIBUZIN) for combating weeds in soy beans; furthermore also 2-chloro-N-{[(4-methoxy-6-methyl-1,3,5-triazin-2-yl)-amino]-carbonyl}-benzenesulphonamide (CHLORSULFURON); N,N-dimethyl-N,-(3-chloro-4-methylpheny)-urea (CHLORTOLURON); 4-amino-6-t-butyl-3-ethylthio-1,2,4-triazin-5(4H)-one (ETHIOZIN); methyl 2-[4,5-dihydro-4-methyl-4-(1-methylethyl)-5-oxo-lH-imidazol-2-yl]-4(5)-methylbenzoate (IMAZAMETHABENZ); N,N-dimethyl-N'-(4-isopropylphenyl)-urea (ISOPROTURON); N-methyl-2-(1,3-benzothiazol-2-yloxy-acetanilide (MEFENACET); 2-{[[((4-methoxy-6-methyl-1,3,5-triazin-2-yl)-amino)-carbonyl]-amino]-sulphonyl}-benzoic acid or its methyl (METSULFURON); N-(1-ethylpropyl)-3,4-dimethyl-2,6-dinitroaniline (PENDIMETHALIN); 4-ethylamino-2-t-butylamino-6-methylthio-s-triazine (TERBUTRYNE); methyl 3-8 [[[(4-methoxy-6-methyl-1,3,5-triazin-2-yl)-amino]-carbonyl]-amino]-sulphonyl]-thiophene-2-carboxylate (THLAMETURON); 5-(2,3,3-trichloroallyl) N,N-diisopropylthiolcarbamate (TRI-ALLATE); 2,6-dinitro-4-trifluoromethyl-N,N-dipropylaniline (TRIFLURALIN). Surprisingly, some mixtures also show synergistic action.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

Example 1

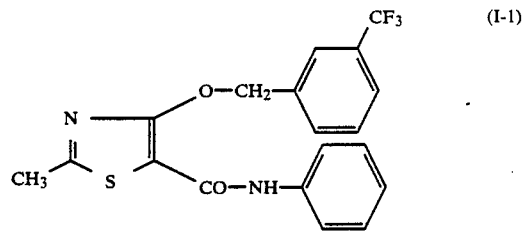

1.1 g of triethylamine is added to a solution of 3.46 g (0.01 mol) of 2-methyl-4-(3-trifluoromethylbenzyloxy)-thiazole-5-carbonyl chloride (see Example II-1) in 50 ml of absolute tetrahydrofuran, and 0.93 g (0.01 mol) of aniline is subsequently added dropwise. The mixture is refluxed for 2 hours, the volatile constituents are distilled off in vacuo, water is added to the residue, and the mixture is extracted using dichloromethane. The extract is dried (over MgSO₄), and the solvent is then removed in vacuo.

2.78 g (71 % of theory) of 2-methyl-4-(3-trifluoromethyl-benzyloxy)-thiazole-5-carboxanilide (I-1) are obtained;

Melting point: 113° C.

The compounds of the general formula (I)

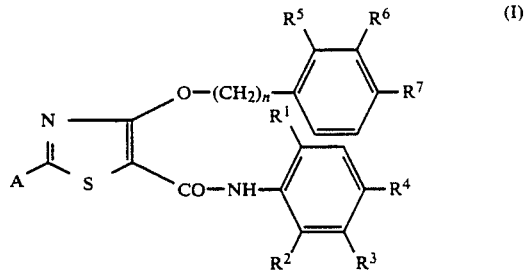

which are listed in Table 1 below can also be prepared analogously to Example 1 and following the general description of the preparation process according to the invention:

TABLE 1

Examples of compounds of the formula (I)

| Example No. | A | n | $R^1$ | $R^2$ | $R^3$ | $R^4$ | $R^5$ | $R^6$ | $R^7$ | Yield (% of theory) | Melting point (°C.) |
|---|---|---|---|---|---|---|---|---|---|---|---|
| (I-2) | $CH_3$ | 0 | F | H | H | F | H | $CF_3$ | H | 89 | 147 |
| (I-3) | $CH_3$ | 1 | Cl | H | H | Cl | H | $CF_3$ | H | 86 | 115 |
| (I-4) | $CH_3$ | 1 | F | H | H | F | H | $CF_3$ | H | 92 | 102 |
| (I-5) | $CH_3$ | 1 | H | H | $CF_3$ | H | H | $CF_3$ | H | 95 | 142 |
| (I-6) | $CH_3$ | 1 | H | H | H | H | H | $CF_3$ | H | 69 | 124[1] |
| (I-7) | $CH_3$ | 1 | Cl | H | H | Cl | $CF_3$ | H | H | 63 | 134[1] |
| (I-8) | $CH_3$ | 1 | F | H | H | F | $CF_3$ | H | H | 68 | 120[1] |
| (I-9) | $CH_3$ | 0 | H | H | H | H | H | $CF_3$ | $NO_2$ | 53 | 174 |
| (I-10) | $CH_3$ | 0 | F | H | H | F | H | $CF_3$ | $NO_2$ | 37 | 174 |
| (I-11) | $CH_3$ | 0 | H | H | $CF_3$ | H | H | $CF_3$ | $NO_2$ | 54 | 170 |
| (I-12) | $CH_3$ | 0 | Cl | H | H | Cl | H | $CF_3$ | $NO_2$ | 64 | 178 |
| (I-13) | $CH_3$ | 0 | H | H | H | H | H | $CF_3$ | H | 80 | 145 |
| (I-14) | $CH_3$ | 0 | F | H | H | H | H | $CF_3$ | H | 97 | 141 |
| (I-15) | $CH_3$ | 0 | F | H | H | H | H | $CF_3$ | H | 89 | 153 |
| (I-16) | $CH_3$ | 0 | Cl | H | H | Cl | H | $CF_3$ | H | 83 | 152 |
| (I-17) | $C_6H_5$ | 0 | F | H | H | F | H | $CF_3$ | H | 76 | 169 |
| (I-18) | $C_2H_5$ | 0 | F | H | H | F | H | $CF_3$ | H | 80 | 117 |
| (I-19) | $C_2H_5$ | 0 | F | H | H | H | H | $CF_3$ | H | 76 | 119 |
| (I-20) | $C_2H_5$ | 0 | H | H | H | F | H | $CF_3$ | H | 72 | 99 |
| (I-21) | $C_2H_5$ | 0 | F | F | H | H | H | $CF_3$ | H | 78 | 110 |
| (I-22) | $CH_3$ | 0 | H | H | H | F | H | $CF_3$ | H | 83 | 151 |
| (I-23) | $C_3H_7$-i | 0 | F | H | H | F | H | $CF_3$ | H | 85 | |
| (I-24) | $C_3H_7$-i | 0 | H | H | H | F | H | $CF_3$ | H | | |
| (I-25) | $C_3H_7$-i | 0 | F | H | H | H | H | $CF_3$ | H | | |
| (I-26) | $C_3H_7$-i | 0 | F | F | H | H | H | $CF_3$ | H | | |
| (I-27) | $C_3H_7$-i | 0 | Cl | H | H | Cl | H | $CF_3$ | H | | |
| (I-28) | $C_3H_7$-i | 0 | H | H | H | Cl | H | $CF_3$ | H | | |
| (I-29) | $C_3H_7$-n | 0 | F | H | H | F | H | $CF_3$ | H | 81 | |
| (I-30) | $C_3H_7$-n | 0 | H | H | H | F | H | $CF_3$ | H | | |
| (I-31) | $C_3H_7$-n | 0 | F | H | H | H | H | $CF_3$ | H | | |
| (I-32) | $C_3H_7$-n | 0 | F | F | H | H | H | $CF_3$ | H | | |
| (I-33) | $C_3H_7$-n | 0 | Cl | H | H | Cl | H | $CF_3$ | H | | |
| (I-34) | $C_3H_7$-n | 0 | H | H | H | Cl | H | $CF_3$ | H | | |

[1] After purification of the crude product by chromatography on silica gel with ethyl acetate/cyclohexane (1:2) as the eluent.

PREPARATION OF THE STARTING SUBSTANCE OF THE FORMULA (IV)

Example (IV-1)

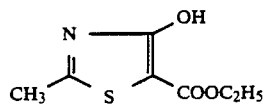

168 g (0.1 mol) of diethyl 2-bromo-malonate are added to 52.5 g (0.1 mol) of thioacetamide in 400 ml of toluene, and the mixture is refluxed for 1 hour. When cold, the solution is decanted off from the undissolved oily residue and evaporated in vacuo. The solid residue which remains is stirred with 500 ml of water, filtered off with suction, washed first with water and then with petroleum ether, and dried.

41 g (31 % of theory) of 2-methyl-5-ethoxy-carbonyl-4-hydroxy-thiazole are obtained;

Melting point: 106°–107° C. (colourless crystals)

Example (IV-2)

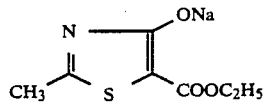

A solution of 3.4 g (0.05 mol) of sodium ethylate (obtained from 1.15 g (0.05 mol) of sodium) in 30 ml of ethanol is added dropwise to a solution of 9.35 g (0.05 mol) of 2-methyl-5-ethoxycarbonyl-4-hydroxy-thiazole (prepared according to Example IV-1) in 75 ml of absolute ethanol. Stirring is continued for 15 minutes at 40°–45° C., the solid is filtered off with suction and washed with petroleum ether, and the resulting product is dried.

10.1 g (96.7% of theory) of the sodium salt of 2-methyl-5-ethoxycarbonyl-4-hydroxy-thiazole are obtained;

Melting point: >250° C.

The compounds of the formula (IV) which are listed in Table 2 below are also obtained analogously to Examples (IV-1) and (IV-2):

TABLE 2

Compounds of the formula (IV)

| Example No. | A | $R^8$ | Z | Yield (% of th.) | m.p. (°C.) |
|---|---|---|---|---|---|
| (IV-3) | $C_6H_5$ | $C_2H_5$ | H | 28 | 89–90 |
| (IV-4) | ![CH3-pyrimidine] | $C_2H_5$ | H | 65 | >250 |
| (IV-5) | $C_2H_5$ | $C_2H_5$ | H | 31 | 88–89 |
| (IV-6) | $C_6H_5$ | $C_2H_5$ | Na | 97 | >250 |
| (IV-7) | ![CH3-pyrimidine] | $C_2H_5$ | Na | 96 | 248–250 (decomp.) |

TABLE 2-continued

| | Compounds of the formula (IV) | | | | |
|---|---|---|---|---|---|
| Example No. | A | R[8] | Z | Yield (% of th.) | m.p. (°C.) |
| (IV-8) | $C_2H_5$ | $C_2H_5$ | Na | 31 | >250 |
| (IV-9) | $C_3H_7$-i | $C_2H_5$ | H | 38 | 45–46 |
| (IV-10) | $C_3H_7$-n | $C_2H_5$ | H | 34 | 49–50 |
| (IV-11) | $C_3H_7$-i | $C_2H_5$ | Na | 76 | >250 |
| (IV-12) | $C_3H_7$-n | $C_2H_5$ | Na | 89 | >250 |

PREPARATION OF THE INTERMEDIATES OF THE FORMULA (VI)

Example (VI-1)

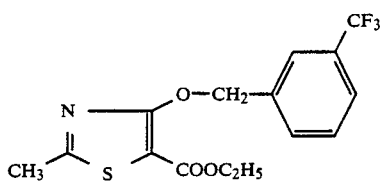

63 g (0.32 mol) of 3-trifluoromethylbenzyl chloride are added dropwise at room temperature to a solution of 67.5 g (0.32 mol) of the sodium salt of 2-methyl-5-ethoxycarbonyl-4-hydroxy-thiazole (cf. Example IV-2) in 180 ml of N-methylpyrrolidone (NMP). The mixture is subsequently heated at 110° C. for 4 hours; when cold, the reaction mixture is poured into 1.5 l of water and extracted with toluene. The organic phase is washed repeatedly with water and then dried (over MgSO4); the mixture is filtered, the solvent is distilled off in vacuo, and the residue which remains is likewise distilled in vacuo.

59 g (53 % of theory) of 2-methyl-5-ethoxy-carbonyl-4-(3-trifluoromethylbenzyloxy)-thiazole are obtained;
Boiling point: 220° C./0.1 mbar;
Melting point of the pure solidified product: 65° C.

Example (VI-2)

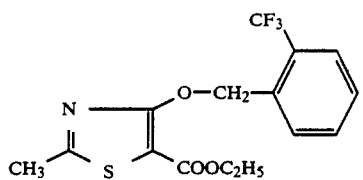

2-Methyl-5-ethoxycarbonyl-4-(2-trifluoromethylbenzyloxy)-thiazole is obtained analogously to Example (VI-1);
Yield: 70% of theory
Melting point: 73° C.

Example (VI-3)

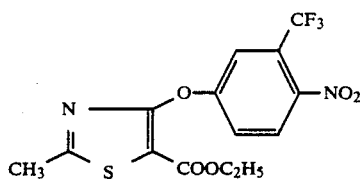

69.5 g (0.33 mol) of 2-nitro-5-fluoro-benzotrifluoride are added dropwise at 100° C. to 69.5 g (0.33 mol) of the sodium salt of 2-methyl-5-ethoxycarbonyl-4-hydroxy-thiazole (cf. Example IV-2) in 250 ml of N-methylpyrrolidone. Stirring is subsequently continued for 16 hours at 100° C., the cooled reaction mixture is poured into 3 l of ice-water and extracted twice using 500 ml portions of toluene, and the combined toluene phases are washed with 1 l of ice-water. After the mixture has been dried (over MgSO4), it is concentrated in vacuo, and the dark crude mixture which remains is filtered chromatographically through silica gel using toluene/ethanol (19:1). After the mixture has been evaporated in vacuo, the crude product is chromatographed on silica gel (eluent: toluene).

35 g (28% of theory) of 2-methyl-5-ethoxycarbonyl-4-(4-nitro-3-trifluoromethyl-phenyloxy)-thiazole are obtained;
Melting point: 82°–83° C.

Example (VI-4)

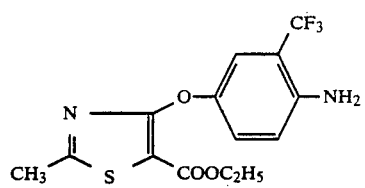

10 g (0.027 mol) of 2-methyl-5-ethoxycarbonyl-4-(4-nitro-3-trifluoromethyl-phenyloxy)-thiazole (cf. Example IV-3) in 200 ml of methanol are hydrogenated at 60° C. and 50–60 bar H2 pressure, 3 g of Raney nickel having been added. After the catalyst has been removed and the solvent has been evaporated in vacuo, 8 g (87 % of theory) of 2-methyl-5-ethoxycarbonyl-4-(4-amino-3-trifluoromethyl-phenyloxy)-thiazole are obtained; melting point: 98° C.

Example (VI-5)

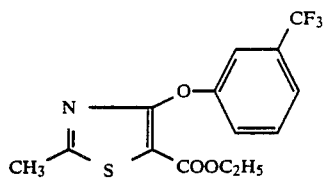

1.4 g of NaNO2 in 30 ml of water are added dropwise with ice cooling in the course of about 20 minutes to 7 g (0.02 mol) of 2-methyl-5-ethoxycarbonyl-4-(4-amino-3-trifluoromethyl-phenoxy)-thiazole (cf. Example (IV-4) in 40 ml of concentrated hydrochloric acid. After the mixture has been stirred for 5 minutes, 300 ml of ethanol are added, and the mixture is then heated slowly to reflux temperature and refluxed for 30 minutes. The volatile constituents are subsequently removed in vacuo, the oil which remains is then taken up in 50 ml of water, a pH of 8 is established by adding dilute sodium hydroxide solution, the mixture is extracted twice with dichloromethane, the extract is dried (over MgSO4) and evaporated in vacuo, and the crude product which remains is filtered chromatographically through silica gel (eluent: toluene). 5.6 g (83.6 % of theory) of 2-methyl-5-ethoxycarbonyl-4-(3-trifluoromethyl-phenyloxy)-thiazole are obtained; melting point: 56° C.

Example (VI-6)

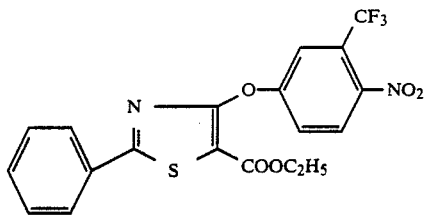

The sodium salt of 2-phenyl-5-ethoxycarbonyl-4-hydroxy-thiazole (cf. Example IV-6) is reacted with 2-nitro-5-fluoro-benzotrifluoride analogously to Example (VI-3). 2-Phenyl-5-ethoxycarbonyl-4-(4-nitro-3-trifluoromethyl-phenyloxy)-thiazole is obtained;

Yield: 23% of theory
Melting point: 117° C.

Example (VI-7)

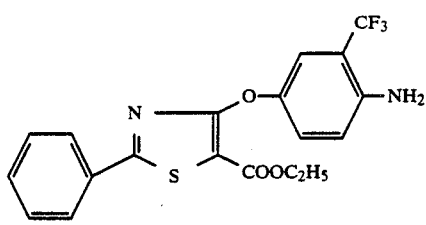

2-Phenyl-5-ethoxycarbonyl-4-(4-amino-3-trifluoromethyl-phenyloxy)-thiazole is obtained analogously to Example (VI-4) by catalytic hydrogenation of 2-phenyl-5-ethoxycarbonyl-4-(4-nitro-3-trifluoromethyl-phenyloxy)-thiazole (cf. Example VI-6);

Yield: 76.5% of theory
Melting point: 125° C.

Example (VI-8)

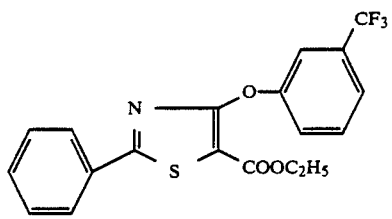

2-Phenyl-5-ethoxycarbonyl-4-(3-trifluoromethyl-phenyloxy)-thiazole is obtained analogously to Example (VI-5) from 2-phenyl-5-ethoxycarbonyl-4-(4-amino-3-trifluoromethyl-phenyloxy)-thiazole (cf. Example VI-7) by diazotization and boiling;

Yield: 79% of theory
Melting point: 166°–167° C.

Example (VI-9)

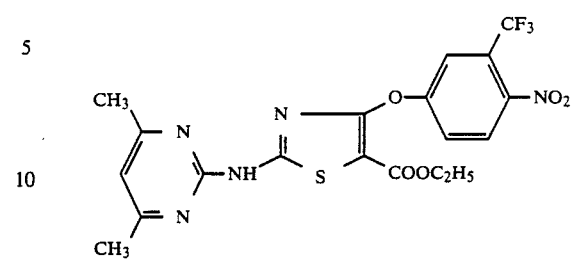

Analogously to Example (VI-3), the sodium salt of 2-(4,6-dimethyl-pyrimidin-2-ylamino)-5-ethoxycarbonyl-4-hydroxy-thiazole (cf. Example IV-7) is reacted with 2-nitro-5-fluoro-benzotrifluoride.

2-(4,6-Dimethyl-pyrimidin-2-ylamino)-5-ethoxycarbonyl-4-(4-nitro-3-trifluoromethyl-phenyloxy)-thiazole is obtained;

Yield: 13% of theory
Melting point: 123° C. (decomposition)

Example (VI-10)

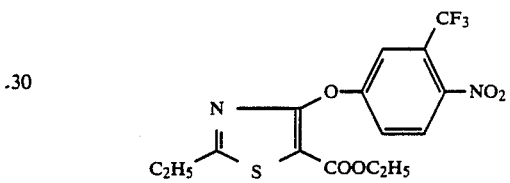

Analogously to Example (VI-3), the sodium salt of 2-ethyl-5-ethoxycarbonyl-4-hydroxy-thiazole (cf. Example IV-8) is reacted with 2-nitro-5-fluoro-benzotrifluoride.

2-Ethyl-5-ethoxycarbonyl-4-(4-nitro-3-trifluoromethyl-phenyloxy)-thiazole is obtained;

Yield: 19% of theory
Melting point: 119°–120° C.

Example (VI-11)

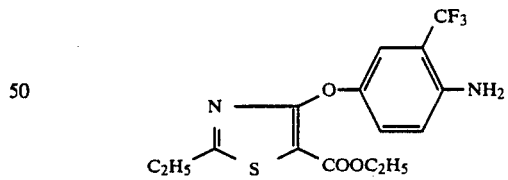

Analogously to Example (VI-4), 2-ethyl-5-ethoxycarbonyl-4-(4-amino-3-trifluoromethyl-phenyloxy)-thiazole is obtained by catalytic hydrogenation of the nitro compound (VI-10);

Yield: 87% of theory
The product is obtained as an oil and is characterized by its $^1$H-NMR spectrum (in CDCl$_3$ with tetramethylsilane (TMS) as the internal standard):

δ = 1.30 ppm (2—C$\underline{H}_3$—CH$_2$—);
δ = 1.36 ppm (—COOCH$_2$—C$\underline{H}_3$);
δ = 2.95 ppm (2—CH$_3$—C$\underline{H}_2$—);
δ = 4,31 ppm (—COOC$\underline{H}_2$—CH$_3$);
δ = 7.3–8.0 ppm (3 aromatic H atoms).

Example (VI-12)

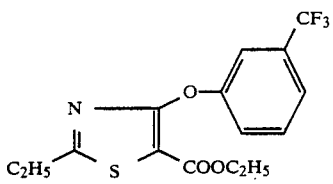

Analogously to Example (VI-5), 2-ethyl-5-ethoxycarbonyl-4-(3-trifluoromethyl-phenyloxy)-thiazole is obtained from the amino compound (VI-11) by diazotization and boiling;

Yield: 81% of theory

The oily product is likewise characterized by its $^1$H-NMR spectrum: The spectrum (measurement conditions identical to those in Example (VI-11)) resembles that of the starting compound (VI-11) with regard to the ethyl groups, while the aromatic protons in the range of δ=7.3–8.0 ppm indicate 4 H atoms.

Example (VI-13)

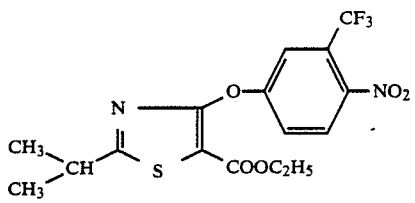

The sodium salt of 2-isopropyl-5-ethoxycarbonyl-4-hydroxy-thiazole (cf. Example IV-11) is reacted with 2-nitro-5-fluoro-benzotrifluoride analogously to Example (VI-3). 2-isopropyl-5-ethoxycarbonyl-4-(4-nitro-3-trifluoromethyl-phenyloxy)-thiazole is obtained;

Yield: 16% of theory.

The product is characterized by its $^1$H-NMR spectrum (in CDCl$_3$ with TMS as the internal standard):

δ=1.32 ppm (—COOCH$_2$—C$\underline{H}_3$);
δ=1.35 ppm [—CH(C$\underline{H}_3$)$_2$];
δ=3.20 ppm [—C$\underline{H}$(CH$_3$)$_2$];
δ=4.30 ppm (—COOC$\underline{H}_2$—CH$_3$);
δ=7.05–8.0 ppm (3 aromatic H atoms).

Example (VI-14)

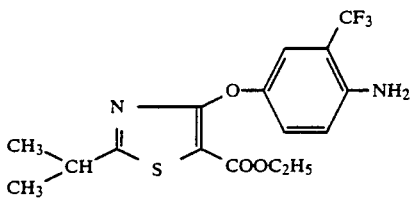

Analogously to Example (VI-4), 2-isopropyl-5-ethoxycarbonyl-4-(4-amino-3-trifluoromethyl-phenyloxy)-thiazole is obtained by catalytic hydrogenation of the nitro compound (VI-13);

Yield: 93% of theory.

$^1$H-NMR spectrum in CDCl$_3$/ with TMS):
δ=1.30 ppm (—COOCH$_2$—C$\underline{H}_3$);
δ=1.33 ppm [—CH(C$\underline{H}_3$)$_2$];
δ=3.15 ppm [—C$\underline{H}$(CH$_3$)$_2$];
δ=4.30 ppm (—COOC$\underline{H}_2$-CH$_3$);
δ=7.2–7.8 ppm (3 aromatic H atoms).

Example (VI-15)

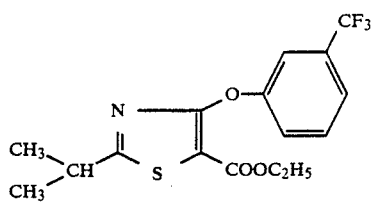

Analogously to Example (VI-5), 2-isopropyl-5-ethoxycarbonyl-4-(3-trifluoromethyl-phenyloxy)-thiazole is obtained from the amino compound (VI-14) by diazotization and boiling;

Yield: 91% of theory.

$^1$H-NMR spectrum (in CDCl$_3$/with TMS):
δ=1.32 ppm [—CH(C$\underline{H}_3$)$_2$];
δ=1.35 ppm (—COOCH$_2$—C$\underline{H}_3$);
δ=3.20 ppm [—C$\underline{H}$(CH$_3$)$_2$];
δ=4.30 ppm (—COOC$\underline{H}_2$—CH$_3$);
δ=7.20–7.5 ppm (3 aromatic H atoms).

Example (VI-16)

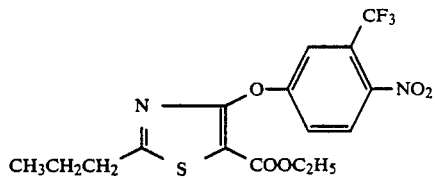

The sodium salt of 2-propyl-5-ethoxycarbonyl-4-hydroxy-thiazole (cf. Example IV-12) is reacted with 2-nitro-5-fluoro-benzotrifluoride analogously to Example (VI-3). 2-Propyl-5-ethoxycarbonyl-4-(4-nitro-3-trifluoromethyl-phenyloxy)-thiazole is obtained;

Yield: 21% of theory.

$^1$H-NMR spectrum (in CDCl$_3$/ with TMS):
δ=1.20–2.65 ppm (7 propyl H atoms);
δ=1.30 ppm (—COOCH$_2$—C$\underline{H}_3$);
δ=4.25 ppm (—COOC$\underline{H}_2$—CH$_3$);
=δ7.1–7.9 ppm (3 aromatic H atoms).

Example (VI-17)

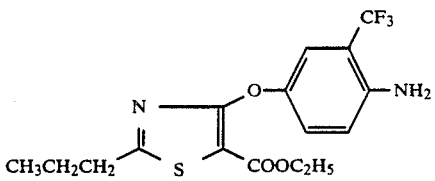

Analogously to Example (VI-4), 2-propyl-5-ethoxycarbonyl-4-(4-amino-3-trifluoromethyl-phenyloxy)-thiazole is obtained by catalytic hydrogenation of the nitro compound (VI-16);

Yield: 88% of theory.

$^1$H-NMR spectrum (in CDCl$_3$/ with TMS):
δ=1.15–2.63 ppm (7 propyl H atoms);
δ=1.28 ppm (—COOCH$_2$—C$\underline{H}_3$);
δ=4.25 ppm (—COOC$\underline{H}_2$—CH$_3$);
δ=7.27–7.8 ppm (3 aromatic H atoms).

Example (VI-18)

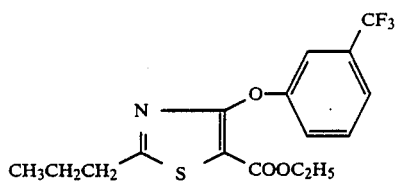

Analogously to Example (VI-5), 2-propyl-5-ethoxycarbonyl-4-(3-trifluoromethyl-phenyloxy)-thiazole is obtained from the amino compound (VI-17) by diazotization and boiling;

Yield: 89% of theory.

$^1$H-NMR spectrum in CDCl$_3$/ TMS):

δ=1.20–2.70 ppm (7 propyl H atoms);
δ=1.28 ppm (—COOCH$_2$—C$\underline{H}_3$);
δ=4.23 ppm (—COOC$\underline{H}_2$—CH$_3$);
δ=7.28–7.53 ppm (4 aromatic H atoms).

PREPARATION OF THE INTERMEDIATES OF THE FORMULA (VII) Example (VII-1)

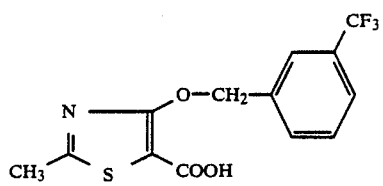

An aqueous solution of 16.8 g of potassium hydroxide is added to 26 g (0.075 mol) of 2-methyl-5-ethoxycarbonyl-4-(3-trifluoromethyl-benzyloxy)-thiazole (cf. Example VI-1) in 300 ml of methanol. The mixture is stirred for 12 hours at room temperature and then concentrated in vacuo, water is added, and the mixture is extracted using dichloromethane. A pH of 1 is established in the aqueous phase with dilute hydrochloric acid, and the acid which has precipitated is filtered off with suction, washed with water and dried.

18 g (76 % of theory) of 2-methyl-5-carboxy-4-(3-trifluoromethyl-benzyloxy)-thiazole are obtained;

Melting point: 149° C.

The compounds of the general formula (VII) which are listed in Table 3 below can also be prepared analogously to Example (VII-1):

TABLE 3
Compounds of the general formula (VII)

| Example No. | A | n | R$^5$ | R$^6$ | R$^7$ | Yield (% of theory) | Melting point (°C.) |
|---|---|---|---|---|---|---|---|
| (VII-2) | CH$_3$ | 1 | CF$_3$ | H | H | 82 | 183 |
| (VII-3) | CH$_3$ | 0 | H | CF$_3$ | NO$_2$ | 70 | 152 |
| (VII-4) | CH$_3$ | 0 | H | CF$_3$ | H | 89 | 155 |
| (VII-5) | C$_6$H$_5$ | 0 | H | CF$_3$ | H | 81 | 195–196 |
| (VII-6) | C$_2$H$_5$ | 0 | H | CF$_3$ | H | 88 | NMR* |
| (VII-7) | C$_3$H$_7$-i | 0 | H | CF$_3$ | H | 83 | NMR** |
| (VII-8) | C$_3$H$_7$-n | 0 | H | CF$_3$ | H | 78 | NMR*** |

*$^1$H-NMR spectrum (in CDCl$_3$, TMS as the internal standard):

δ = 1.31 ppm (2-C$\underline{H}_3$—CH$_2$—); δ = 3.0 ppm (2-CH$_3$—C$\underline{H}_2$—);
δ = 7.3–8.0 ppm (4 aromatic H atoms)

**$^1$H-NMR spectrum (in CDCl$_3$ with TMS as the internal standard):

δ = 1.37 ppm [—CH(C$\underline{H}_3$)$_2$]; δ = 3.18 ppm [—C$\underline{H}$(CH$_3$)$_2$];
δ = 7.2–7.8 ppm (4 aromatic H atoms).

***$^1$H-NMR spectrum (in CDCl$_3$ with TMS as the internal standard):

δ = 2.90–1.22 ppm (7 propyl H atoms);

PREPARATION OF THE INTERMEDIATES OF THE FORMULA (II)

Example (II-1)

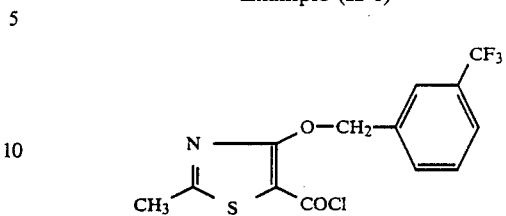

11.9 g (0.01 mol) of thionyl chloride are added dropwise at room temperature with stirring to 16.75 g (0.05 mol) of 2-methyl-5-carboxy-4-(3-trifluoromethyl-benzyloxy)-thiazole (cf. Example (VII-1)) in 200 ml of dichloromethane.

The reaction mixture is then refluxed for 2 hours and subsequently evaporated in vacuo.

13.8 g (89 % of theory) of 2-methyl-4-(3-trifluoromethyl-benzyloxy)-thiazole-5-carbonyl chloride are obtained as the residue.

The compound (II-1) was characterized by mass spectroscopy (M+: 345/347).

The compounds of the general formula (II) which are listed in Table 4 below can also be prepared analogously to Example (II-1):

TABLE 4
Compounds of the general formula (II)

| Example No. | A | n | X | R$^5$ | R$^6$ | R$^7$ | Yield (% of theory) | Mass spectrum (M$^+$) |
|---|---|---|---|---|---|---|---|---|
| (II-2) | CH$_3$ | 1 | Cl | CF$_3$ | H | H | 92 | 345/347 |
| (II-3) | CH$_3$ | 0 | Cl | H | CF$_3$ | NO$_2$ | 91 | 366/368 Melting point |
| (II-4) | CH$_3$ | 0 | Cl | H | CF$_3$ | H | 81 | 80° C. |
| (II-5) | C$_6$H$_5$ | 0 | Cl | H | CF$_3$ | H | 87 | 135° C. Mass spectrum (M$^+$) |
| (II-6) | C$_2$H$_5$ | 0 | Cl | H | CF$_3$ | H | 85 | 335/337 |
| (II-7) | C$_3$H$_7$-i | 0 | Cl | H | CF$_3$ | H | 93 | 349/351 |
| (II-8) | C$_3$H$_7$-n | 0 | Cl | H | CF$_3$ | H | 88 | 349/351 |

USE EXAMPLES

In the use examples which follow, the compound which is indicated below and belongs to the prior art is used as comparison substance:

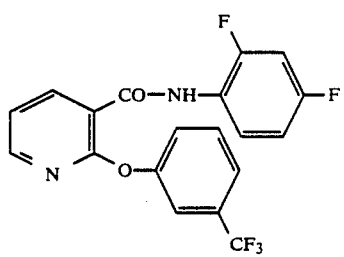

N-(2,4-difluorophenyl)-2-(3-trifluoromethyl-phenoxy)-3-pyridinecarboxamide (DIFLUFENICAN) (known from EP-A-53,011).

Example A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

This test shows that for example the compounds of Preparation Examples (I-2) and (I-22) are better tolerated by wheat and markedly more effective against weeds than the previously known comparison agent diflufenican.

Example B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 1,000 l of water/ha. After three weeks, the degree of damage to the plants is rated in % damage in comparison to the development of the untreated control.

The figures denote:
0% = no action (like untreated control)
100% = total destruction In this test, too, the compounds of the formula (I) according to the invention show a very good action.

It will be appreciated that the instant specification is set forth by way of illustration and not limitation, and that various modifications and changes may be made without departing from the spirit and scope of the present invention.

What is claimed is:

1. A thiazolecarboxamide derivative of the formula

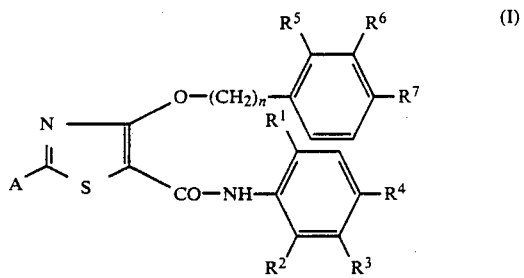

in which
n represents the numbers 0 or 1,
A represents $C_1$-$C_{10}$-alkyl, phenyl, furanyl, thienyl, pyrrolyl, thiazolyl, oxazolyl, pyrazolyl, imidazolyl, pyridyl, pyrimidinyl, phenylamino, pyridylamino or pyrimidinylamino, it being possible for these radicals to be substituted by halogen or (with the exception of alkyl) by $C_1$-$C_4$-alkyl,
$R^1$ represents hydrogen, fluorine, chlorine or $C_1$-$C_4$-alkyl,
$R^2$ represents hydrogen, fluorine, chlorine or $C_1$-$C_4$-alkyl,
$R^3$ represents hydrogen, fluorine or chlorine, or represents $C_1$-$C_4$-alkyl which is optionally monosubstituted or polysubstituted by at least one of fluorine and chlorine,
$R^4$ represents hydrogen, fluorine or chlorine, or represents $C_1$-$C_4$-alkyl which is optionally monosubstituted or polysubstituted by at least one of fluorine and chlorine,
$R^5$ represents hydrogen, fluorine, chlorine, $C_1$-$C_4$-alkyl, nitro or amino,
$R^6$ represents hydrogen, fluorine or chlorine, or represents $C_1$-$C_4$-alkyl, $C_1$-$C_4$-alkoxy or $C_1$-$C_4$-alkylthio, each of which is optionally monosubstituted or polysubstituted by at least one of fluorine and chlorine or represents $C_2$-$C_5$-alkoxycarbonyl, and
$R^7$ represents hydrogen, fluorine, chlorine, $C_1$-$C_4$-alkyl, nitro or amino.

2. A thiazolecarboxamide derivative according to claim 1, in which
n represents the numbers 0 or 1,
A represents $C_1$-$C_3$-alkyl, phenyl, furanyl, thienyl, pyrrolyl, thiazolyl, oxazolyl, pyrazolyl, imidazolyl, pyridyl, pyrimidinyl, phenylamino, pyridylamino or pyrimidinylamino, it being possible for these radicals to be substituted by fluorine or chlorine or (with the exception of alkyl) by methyl or ethyl;
$R^1$ represents hydrogen, fluorine, chlorine, methyl or ethyl,
$R^2$ represents hydrogen, fluorine, chlorine, methyl or ethyl,
$R^3$ represents hydrogen, fluorine or chlorine, or represents methyl or ethyl, each of which is optionally substituted by fluorine or chlorine,
$R^4$ represents hydrogen, fluorine or chlorine, or represents methyl or ethyl, each of which is optionally substituted by fluorine or chlorine,
$R^5$ represents hydrogen, fluorine, chlorine, methyl, ethyl, nitro or amino,
$R^6$ represents hydrogen, fluorine or chlorine, or represents methyl, ethyl, methoxy, ethoxy, methylthio or ethylthio or methoxycarbonyl or ethoxycarbonyl, each of which is optionally substituted by fluorine or chlorine, and R⁷ represents hydrogen, fluorine, chlorine, methyl, ethyl, nitro or amino.

3. A compound according to claim 1, wherein such compound is 2-methyl-4-(3-trifluoromethyl-phenoxy)-5-(2,4-difluorophenylaminocarbonyl) thiazole of the formula

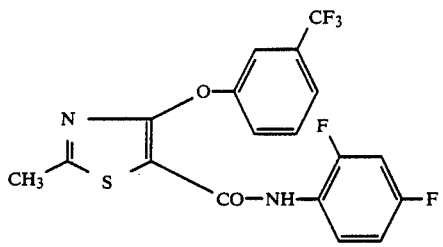

4. A compound according to claim 1, wherein such compound is 2-methyl-4-(3-trifluoromethyl-phenoxy)-5-(4-fluorophenylaminocarbonyl)-thiazole of the formula

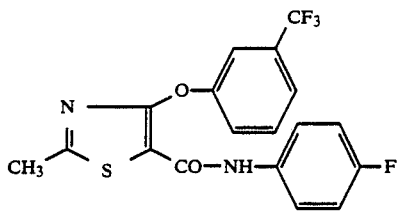

5. A herbicidal composition comprising a herbicidally effective amount of a compound according to claim 1 and a diluent.

6. A method of combating unwanted vegetation which comprises applying to such vegetation or to a locus from which it is desired to exclude such vegetation a herbicidally effective amount of a compound according to claim 1.

7. The method according to claim 6, wherein such compound is
2-methyl-4-(3-trifluoromethyl-phenoxy)-5-(2,4-dlfluorophenylaminocarbonyl)-thiazole, or
2-methyl-4(3-trifluoromethyl-phenoxy)-5-(4-fluorophenylaminocarbonyl)-thiazole.

8. A thiazolecarboxylic acid halide of the formula

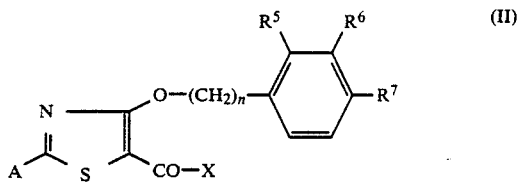

in which
n represents the numbers 0 or 1,
A represents $C_1$–$C_{10}$-alkyl, phenyl, furanyl, thienyl, pyrrolyl, thiazolyl, oxazolyl, pyrazolyl, imidazolyl, pyridyl, pyrimidinyl, phenylamino, pyridylamino or pyrimidinylamine, it being possible for these radicals to be substituted by halogen or (with the exception of alkyl) by $C_1$–$C_4$-alkyl;
R⁵ represents hydrogen, fluorine, chlorine, $C_1$–$C_4$-alkyl, nitro or amino,
R⁶ represents hydrogen, fluorine or chlorine, or represents $C_1$–$C_4$-alkyl, $C_1$–$C_4$-alkoxy or $C_1$–$C_4$-alkylthio, each of which is optionally monosubstituted or polysubstituted by at least one of fluorine and chlorine, or represents $C_2$–$C_5$-alkoxycarbonyl, and
R⁷ represents hydrogen, fluorine, chlorine, $C_1$–$C_4$-alkyl, nitro or amino, and
X represents fluorine, chlorine or bromine.

9. A thiazolecarboxylic acid halide according to claim 8, in which
n represents the numbers 0 or 1,
A represents $C_1$–$C_3$-alkyl, phenyl, furanyl, thienyl, pyrrolyl, thiazolyl, oxazolyl, pyrazolyl, imidizolyl, pyridyl, pyrimidinyl, phenylamino, pyridylamino or pyrimidinylamino, it being possible for these radicals to be substituted by fluorine or chlorine or (with the exception of alkyl) by methyl or ethyl;
R⁵ represents hydrogen, fluorine, chlorine, methyl, ethyl, nitro or amino,
R⁶ represents hydrogen, fluorine or chlorine, or represents methyl, ethyl, methoxy, ethoxy, methylthio or ethylthio or methoxycarbonyl or ethoxycarbonyl, each of which is optionally substituted by fluorine or chlorine, and
R⁷ represents hydrogen, fluorine, chlorine, methyl, ethyl, nitro or amino, and
X represents chlorine or bromine.

* * * * *

UNITED STATES PATENT AND TRADEMARK OFFICE
CERTIFICATE OF CORRECTION

PATENT NO. : 5,057,142

DATED : October 15, 1991

INVENTOR(S) : Baasner et al.

It is certified that error appears in the above-identified patent and that said Letters Patent is hereby corrected as shown below:

Col. 26, line 16   Delete " pyrimidinylamine " and substitute
                   -- pyrimidinylamino --

Signed and Sealed this

Twenty-first Day of September, 1993

Attest:

BRUCE LEHMAN

Attesting Officer          Commissioner of Patents and Trademarks